United States Patent [19]

Kent et al.

[11] Patent Number: 4,461,167
[45] Date of Patent: Jul. 24, 1984

[54] PSYCHROMETER FOR MEASURING THE HUMIDITY OF A GAS FLOW

[75] Inventors: Albert C. Kent; Howard N. Rosen, both of Carbondale, Ill.

[73] Assignee: The United States of America as represented by the Secretary of Agriculture, Washington, D.C.

[21] Appl. No.: 308,747

[22] Filed: Oct. 5, 1981

[51] Int. Cl.[3] ............................................. G01N 25/62
[52] U.S. Cl. ........................................... 73/29; 73/338
[58] Field of Search ............. 73/29, 338, 338.3, 338.6, 73/77; 236/44 A

[56] References Cited

U.S. PATENT DOCUMENTS

| | | | |
|---|---|---|---|
| 1,601,243 | 9/1926 | Irwin, Jr. | 73/338.6 |
| 1,942,934 | 1/1934 | Reeve | 73/29 |
| 2,107,077 | 2/1938 | Magner | 73/338 |
| 2,623,391 | 12/1952 | Malecki | 73/338 |
| 3,196,683 | 7/1965 | Gross | 73/338 |
| 3,459,034 | 8/1969 | Kawaguchi | 73/338.6 |
| 3,515,001 | 6/1970 | Greenspan et al. | 73/338.6 |
| 3,603,135 | 9/1971 | Kawaguchi | 73/29 |
| 3,886,797 | 6/1975 | Bauer | 73/29 |
| 4,129,250 | 12/1978 | Chaikin et al. | 73/77 |
| 4,222,261 | 9/1980 | LeBlanc et al. | 73/29 |

*Primary Examiner*—Stephen A. Kreitman
*Attorney, Agent, or Firm*—M. Howard Silverstein; David G. McConnell

[57] ABSTRACT

In a psychrometer for measuring the humidity of a gas flow, especially a gas flow having a temperature of above 100° C., a flow of liquid is supplied to a wick surrounding the wet sensor via a preheater which heats the liquid to approximately the wet bulb temperature of the gas stream before the liquid comes into contact with the wet sensor, thereby avoiding cooling of the wet sensor by the liquid. The necessary preheating of the liquid can be achieved largely by heat exchange between the liquid and the gas flow downstream of the wet sensor; such heat exchange may be effected in part by using an auxiliary wick from which a portion of the liquid evaporates before the rest of the liquid reaches the main wick.

7 Claims, 3 Drawing Figures

4,461,167

PSYCHROMETER FOR MEASURING THE HUMIDITY OF A GAS FLOW

BACKGROUND OF THE INVENTION

This invention relates to a psychrometer for measuring the humidity (a term which is used herein to mean the degree of saturation with any desired vapor, not merely water vapor) of a gas flow. The instant psychrometer is especially useful for measuring the humidity of gas flows at temperatures of about 93° to about 260° C.

Numerous forms of psychrometer are known in the prior art. The most relevant prior art of which the applicants are aware may be summarized as follows.

U.S. Pat. No. 1,603,243 to Irwin describes an early form of psychrometer in which the incoming air is heated by means of an electric heater. The psychrometer is intended for use at substantially ambient temperatures, the purpose of the heating being to prevent the formation of ice around the wet bulb.

U.S. Pat. No. 1,942,934 to Reeve describes a psychrometer in which a wick passes through a constricted opening so that the main bulk of the water supply to the wick is isolated from the gas stream passing through the psychrometer.

U.S. Pat. No. 2,107,077 to Magner describes a psychrometer in which the wet bulb has a wick surrounded by a sock so that the gas the humidity of which is being measured passes over the sock and keeps the water supplied to the wet bulb at substantially the same temperature as the gas stream. This form of psychrometer is, however, capable of operating only at relatively low temperatures.

U.S. Pat. No. 2,623,391 to Malecki describes a psychrometer in which the wet bulb is surrounded by a mass of porous material to improve thermal conductivity to the wet bulb and thus to secure better sensitivity and quicker response to vapor concentration changes.

U.S. Pat. No. 3,196,683 to Gross describes a psychrometer in which, to prevent excessive evaporation of water from the wick and consequent fouling thereof at the point where the wick is exposed to the air flow, the wick is enclosed within a tube which is split so as to allow only an extremely small area of contact between the wick and the air flow.

U.S. Pat. No. 3,459,034 to Kawaguchi describes a psychrometer for measuring the moisture content of a gas at high temperatures in which a sample of gas is admitted to a measuring chamber and a wet bulb within the chamber is supplied with water from a reservoir which is kept cooled below the boiling point of water.

U.S. Pat. No. 3,515,001 to Greenspan, et al. describes a psychrometer for measuring the humidity of a stream of gas containing vapor of a condensible liquid in which a sample stream of the vapor/gas mixture is flowed over the wick and a heat exchanger, while a stream of liquid corresponding to the condensed vapor of the vapor/gas mixture is counterflowed through the heat exchanger to the wick.

U.S. Pat. No. 3,603,135 to Kawaguchi describes a high-temperature psychrometer in which the wet bulb is detachably inserted into a sleeve made of a temperature-resistant capillary material, the base portion of this sleeve being exposed to the passage of water in a predetermined amount and at a predetermined pressure so that the sleeve is maintained in a reproducably wet condition.

U.S. Pat. No. 3,886,797 to Bauer describes an electrical-resistance psychrometer provided with means for uniform supply of an evaporating liquid from a supply tank to an evaporator body made of a porous material which surrounds the "wet" resistor, this wet resistor having an appreciable electric current passed therethrough so as to increase its temperature.

U.S. Pat. No. 4,129,250 to Chaikin, et al. describes a psychrometer intended for measuring the humidity of exhaust air from industrial driers (and thus capable of operating at moderately high temperatures) in which a wet bulb thermocouple is physically dipped into a bowl of water under the control of a timer system to control the amount of exhaust air discharged until the wet bulb thermocouple is equilibrated with the exhaust air sampled after dipping.

U.S. Pat. No. 4,222,261 issued Sept. 16, 1980 to Leblanc, et al. describes a high-temperature psychrometer in which the wet bulb is surrounded by a sheath of porous material, which is in turn surrounded by a screen to prevent thermal radiation evaporating too much liquid from the sheath. A dosing pump is provided for injecting predetermined amounts of volatile liquid at regular intervals into the interior of the sheath and onto the screens to ensure sufficient moistening of the sheath and the screens.

Zagorzycki, "Automatic Control of Conveyor Driers", Chemical Engineering Practice 75(4), 50 (1979) discusses the drying of food products and the limitations of prior art psychrometers.

Those skilled in the art are aware that dry bulb-wet bulb psychrometers, such as those discussed above, wherein a humid gas stream is passed over a continuously wetted wick and measurements of gas flow temperature (hereinafter referred to as the dry bulb temperature of the gas flow) and wetted wick temperature (hereinafter referred to as the wet bulb temperature of the gas flow) are used to determine humidity, can be used to measure humidity at dry bulb temperatures up to about 121° C., but special precautions are necessary and results are of questionable accuracy above 100° C. The most difficult problem at temperatures above 100° C. is keeping the wick saturated with water and in previous psychrometers intended for use above 100° C., the velocity of the gas flow had to be above about 4.5 m/sec. Also, heat conduction and heat radiation have led to erroneous readings at the higher temperatures.

Dew point cells, using hygroscopic salts such as lithium chloride, are rugged, easy to maintain and can operate up to dry bulb temperatures of about 104° C., but the dew point temperature must not exceed about 80° C. Electronic hygrometers, which change impedence or capacitance with changes in humidity, and optical dew point cells, which use a thermoelectrically-cooled mirror to sense that temperature at which water is in equilibrium with the vapor in the air can only be used up to dry bulb temperatures of about 94° C.

Thus, no really satisfactory method exits for measuring humidity of gas streams having dry bulb temperatures of about 94° to about 260° C. and wet bulb temperatures of about 38° to about 99° C., despite the fact that evaluation of energy content, corrosive properties and chemical composition of air streams necessitate quantitative measurements of the humidity of gas streams within these ranges. The instant invention seeks to provide a psychrometer which is useful within these temperature ranges.

SUMMARY OF THE INVENTION

The invention provides a psychrometer for measuring the humidity (as hereinbefore defined) of a gas flow, this psychrometer comprising a first sensor for measuring the dry bulb temperature of the gas flow, a second sensor for measuring the wet bulb temperature of the gas flow, a wick surrounding the second sensor and capable of absorbing a volatile liquid, liquid supply means for supplying the volatile liquid to the wick adjacent the second sensor and liquid preheater means for heating the volatile liquid to a temperature within about 5 C.° of the wet bulb temperature sensed by the second sensor before the liquid is supplied to the liquid supply means.

Preferably, in the instant psychrometer, the liquid preheater heats the volatile liquid to a temperature within about 2 C.° lower than the wet bulb temperature. Such preheating of the liquid is conveniently achieved by a liquid preheater comprising first preheater means for heating the liquid to a temperature within about 10 C.° of the wet bulb temperature of the gas stream and a second preheater means for receiving liquid from the first preheater means and effecting heat exchange between the liquid and the gas flow.

Furthermore, the instant psychrometer is desirably provided with a gas preheater for heating the gas flow before contact thereof with the sensors of this psychrometer in order to prevent condensation of liquid from the gas flow prior to measurement of its wet bulb temperature by the second sensor. Finally, the instant psychrometer also desirably is provided with means for controlling the gas flow to ensure that the velocity of the gas flow past the first and second sensors is not less than about 1.5 m/sec.

It will of course be appreciated that the volatile liquid supplied to the second sensor of the instant psychrometer must be the same volatile liquid as that whose relative saturation is to be measured in the gas flow. Thus, in the most common application of the instant psychrometer, namely for measuring water vapor in air, the volatile liquid supplied to the second sensor will be water, preferably distilled water in order to prevent clogging of the wick as the water evaporates therefrom.

DESCRIPTION OF THE PREFERRED EMBODIMENT

Figure 1:
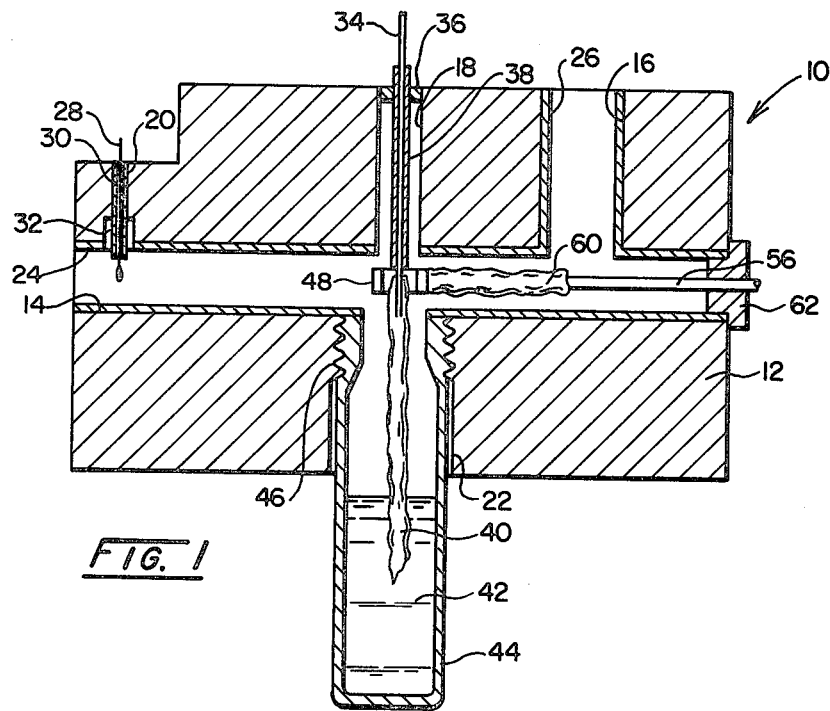
FIG. 1 is a vertical section through a major portion of a preferred psychrometer of the invention.
Figure 2:
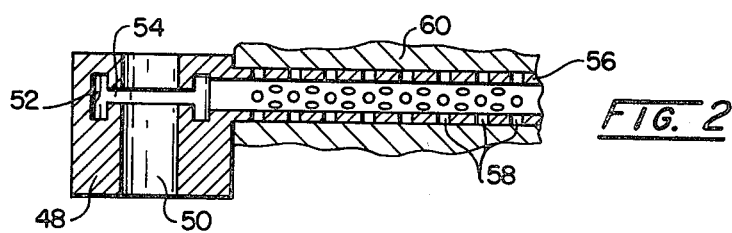
FIG. 2 is a vertical section through the liquid supply means and part of the liquid preheater means of the psychrometer shown in FIG. 1.
Figure 3:
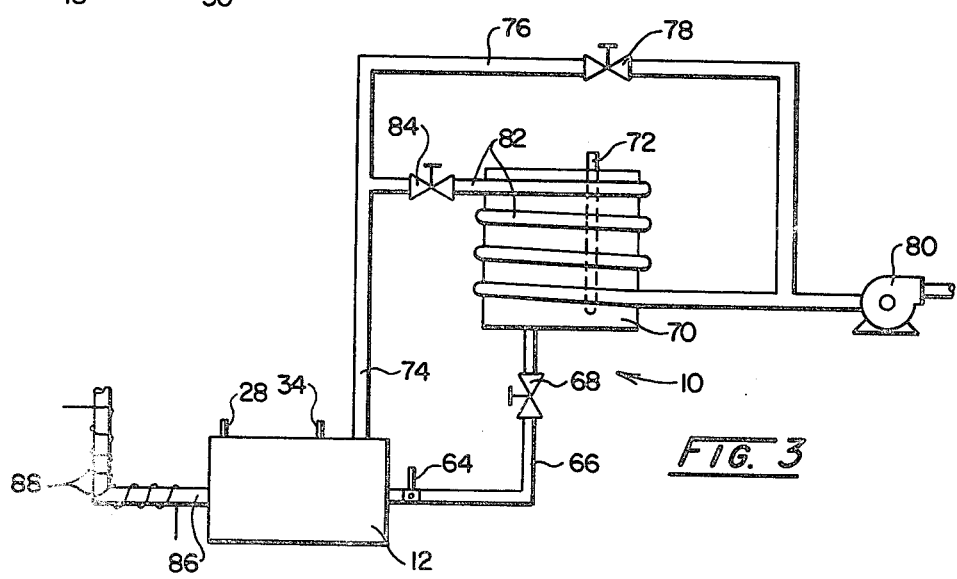
FIG. 3 shows schematically the psychrometer shown in FIG. 1 and associated apparatus used in connection therewith.

The psychrometer (generally designated 10) shown in FIGS. 1-3 comprises a body member 12 formed from a substantially cuboidal block of an insulated, reinforced material. The block 12 is penetrated by five bores, namely a horizontal bore 14, a first vertical bore 16 extending upwardly from the bore 14 through the upper part of the block 12, a second vertical bore 18 extending upwardly from the bore 14 parallel to the bore 16, a narrow third vertical bore 20 extending upwardly from the bore 14 parallel to the bores 16 and 18, and a fourth vertical bore 22 extending downwardly from the bore 14 through the lower part of the block 12, the bore 22 being coaxial with but larger in diameter than the bore 18. The bores 14 and 16 are lined with sleeves 24 and 26 respectively formed of a material of moderately low conductivity and emmissivity, such as stainless steel, the sleeve 24 being provided with apertures communicating with the bores 18, 20 and 22 and the sleeves 24 and 26 being integral with one another where the bores 14 and 16 meet.

The bore 20 accomodates a first sensor in the form of a thermocouple 28 surrounded (except at the sensing tip of the thermocouple) by a thin tube 30. By way of example, the thermocouple 28 may be a 28 gauge type T thermocouple, and the cylinder 30 may be 3.2 mm. in diameter. The lower end of the tube 30 is accommodated within an adapter 32 integral with the sleeve 24. It will seen that the sensing tip of the thermocouple 28 projects into the bore 14 through which the gas flow being measured passes, and can thus sense the dry bulb temperature of the gas flow.

A second sensor, in the form of a thermocouple 34 similar to the thermocouple 28, is accommodated within the bore 18, the upper end of the bore 18 being closed by an adapter 36 in order to prevent leakage of gas therethrough. The major part of the length of the thermocouple 34 is protected by an insulating sleeve 38. A double-layered wick 40 surrounds the lower end of the thermocouple 34 and extends downwardly therefrom into a quantity of liquid 42 held within a reservoir 44 retained within the bore 22 by means of screw threads 46. The wick 40 is kept saturated with liquid and surrounds the sensing tip of the thermocouple 34, which lies within the bore 14 and can thus sense the wet bulb temperature of the gas flow passing through the bore 14.

Liquid is supplied to the upper end of the wick 40 slightly above the sensing tip of the thermocouple 34 by a liquid supply means in the form of a hollow collar 48, best seen in FIG. 2. As shown in FIG. 2, the collar 48 has the form of an annulus of a cylinder, the central bore 50 of the cylinder accommodating the upper end of the wick 40 an the thermocouple 34, neither of which is shown in FIG. 2. Within the body of the collar 48 is formed a toroidal cavity 52 which is linked to the central bore 50 by a narrow slot 54 which encircles the bore 50.

Also as shown in FIG. 2, the toroidal cavity 52 comunicates with the interior of a tube 56, which forms part of the liquid preheater means of the psychrometer. The tube 56 has a plurality of apertures 58 passing through a portion of the tube 56 adjacent the collar 48, and this perforate portion of the tube 56 is surrounded by an auxiliary wick 60 capable of absorbing liquid which leaves the tube 56 via the apertures 58. The auxiliary wick 60 may be formed of materials similar to those of the wick 40.

Reverting to FIG. 1, it will be seen that the perforate portion of the tube 56 surrounded by the auxiliary wick 60 terminates adjacent the lower end of the bore 16 and that the remaining portion of the tube 56, which does not have any apertures passing therethrough, leaves the right-hand end (in FIG. 1) of the bore 14 via an adapter 62. As shown in FIG. 3, that portion of the tube 56 beyond the adapter 62 and thus outside the body member 12 is provided with a water supply temperature sensor 64. The tube 56 is joined via an elbow to a similar tube 66 provided with a liquid supply control valve 68. The end of the tube 66 remote from the tube 56 is in fluid communication with the interior of a liquid reservoir 70 containing a large supply of the liquid to be fed to the wicks 40 and 60. The reservoir 70 is provided with a liquid heater 72 which is thermostatically controlled so as to keep the liquid within the reservoir 70 not more than about 10 C.°, and preferably not more than about 5.5 C.°, below the anticipated wet bulb temperature of the gas flow through the bore 14.

FIG. 3 also shows a gas exhaust line 74 which, although not shown in FIG. 1, is connected in a fluid-tight manner to the sleeve 26 within the bore 16. The line 74 is connected via an elbow to a similar gas by-pass line 76 provided with a by-pass valve 78. After passing through the valve 78, the by-pass line 76 is connected to the input of a vacuum pump 80.

The line 74 communicates not only with the by-pass line 76 but also with a liquid heating line 82 having a helical portion which encircles the reservoir 70. Between the line 74 and the helical portion surrounding the reservoir, the line 82 is provided with a control valve 84, and the end of the line 82 remote from the line 74 is connected to the inlet of the vacuum pump 80. It will be appreciated that the relatively hot gas passing through the line 82 helps to keep the liquid in the reservoir 70 at the proper temperature, and that the valves 78 and 84 can be manipulated to control the proportion of gas leaving the line 74 which passes around the reservoir 70, and thus the amount of heat applied to the reservoir 70 by the line 82.

Finally, FIG. 3 shows a gas inlet line 86 which is integral with the sleeve 24 and through which gas enters the horizontal bore 14. The line 86 is L-shaped and has a heater tape 88 wrapped therearound to heat the air entering the bore 14.

The psychrometer shown in FIG. 1–3 operates as follows. As already mentioned, the heater 72 and the flow of hot gas through the line 82 maintain the liquid in the reservoir 70 at not more than about 5.5 C.° below the anticipated wet temperature of the gas flow. Liquid leaves the reservoir 70 via the line 66 at a rate controlled via the valve 68 and then passes through the line 56 where its temperature is checked by the liquid supply temperature sensor 64. After passing the temperature sensor 64 the liquid passes along the line 56 through the adapter 62 and eventually reaches the perforate part of the line 56 adjacent the collar 48. Some of the liquid then passes through the apertures 58 and is absorbed by the auxiliary wick 60. The liquid thus absorbed by the wick 60 evaporates in the gas flow passing along the bore 14, thereby effecting heat exchange between the gas flow and the liquid within the tube 56. This heat exchange ensures that the liquid reaches the collar 48 at a temperature within about 1 C.° of the wet bulb temperature of the gas.

That portion of the liquid within the tube 56 which does not pass through the apertures 48 eventually passes into the toroidal chamber 52 and is thence sprayed via the narrow slot 54 onto the upper end of the wick 40 adjacent the sensing tip of the thermocouple 34. The major part of the liquid thus sprayed onto the wick 40 is evaporated therefrom by the gas flow passing along the bore 14, thus ensuring that the thermocouple 34 registers the correct wet bulb temperature of the gas flow. The minor portion of the liquid which is not evaporated from the wick 40 passes down the wick and is received into the body of liquid 42 within the reservoir 44.

The gas flow whose humidity is being measured enters the psychrometer via the line 86 and while passing through this line is heated by the heater tape 88 by not more than about 1 C.° to prevent condensation of liquid from the gas flow prior to measurement of the wet bulb temperature of the gas flow by the thermocouple 34. The gas flow then passes along the bore 14, where it evaporates liquid from both wicks 40 and 60 in the manner previously described and then leaves the block 12 via the bore 16. After thus leaving the block 12, the gas flow enters the line 74 and a portion thereof (this proportion being determined by the settings of the valve 78 and 84) passes through the line 82, thereby assisting in the heating of liquid within the reservoir 70, and leaves the psychrometer via the vacuum pump 80. That portion of the gas flow passing through the line 74 which does not enter the line 84 passes via the by-pass line 76 to the vacuum pump 80. The rate of flow through the vacuum pump 80 is adjusted so that the rate of gas flow along the bore 14 past the thermocouples and the wicks is not less than about 1.5 m/sec. since this is about the lowest gas velocity at which the psychrometer gives reliable measurements.

Once the wet and dry bulb temperatures of the gas stream have been measured by the instant psychrometer, the absolute humidity may be calculated from the thermodynamic properties of the gas and liquid vapor in question. Those skilled in the art are aware that for air and water vapor over the range of 200°–500° F. (94°–260° C.) dry gas temperature and 100°–210° F. (38°–99° C.) wet gas temperature, the absolute humidity may be calculated by the equation:

$$H = H_s - \frac{(0.243+).454H_s)(T_{DB} - T_{WB})}{598 + 0.454\,T_{DB} - T_{WB}}.$$

where
H is the absolute humidity of the air-water vapor mixture in kg water/kg dry air
$H_s$ is the absolute humidity of the saturated air-water vapor mixture at the WB temperature in kg water/kg dry air,
$T_{DB}$ is the dry bulb temperature in °C., and
$T_{WB}$ is the wet bulb temperature in °C.

The constants in the above equation are derived from the average values of the thermodynamic values of air and water vapor over the temperature ranges previously mentioned. Values $H_s$ may be obtained from standard tables. It will be apparent to those skilled in the art that similar equations may be calculated for temperatures expressed in 7° and for gas/vapor pairs other than air and water vapor.

Experimental Results

Humid air streams of controlled humidity and temperature were sampled by the instant psychrometer shown in FIGS. 1–3, the dry and wet bulb temperatures being recorded. The humid air streams were also adiabatically mixed with a cooler and less humid air stream such that the mixed air streams had a temperature not exceeding about 77° C. so that the humidity of the mixed streams could be accurately measured with a standard thin-film capacitor relative humidity probe. The humidity of the high temperature gas flows measured by the psychrometer was then calculated from the humidity of the cool stream and the flow rates of the streams which were mixed to produce the lower-temperature stream actually measured. The humidities as measured by the instant psychrometer and those calculated from the humidity probe measurements are set forth in the table below:

| Dry temperature: °C. | Wet temperature: °C. | Humidity, kg water/kg dry air | | |
|---|---|---|---|---|
| | | Psychrometer: | Calculated: | Difference |
| 22.8 | 15.0 | 0.0070 | 0.0074 | −0.0004 |
| 116.1 | 37.8 | 0.0097 | 0.0096 | 0.0001 |
| 101.1 | 35.6 | 0.0099 | 0.0100 | −0.0001 |
| 116.1 | 47.8 | 0.0444 | 0.0450 | −0.0006 |
| 115.6 | 50.0 | 0.0545 | 0.0560 | −0.0015 |
| 103.9 | 56.1 | 0.0991 | 0.0985 | 0.0006 |
| 104.4 | 58.9 | 0.141 | 0.120 | 0.021 |
| 137.2 | 65.6 | 0.163 | 0.172 | −0.009 |
| 150 | 67.2 | 0.190 | 0.187 | 0.003 |
| 128.3 | 67.2 | 0.193 | 0.199 | −0.006 |
| 150.5 | 81.1 | 0.483 | 0.541 | −0.058 |
| 177.2 | 83.3 | 0.708 | 0.632 | 0.076 |
| 109.4 | 90.6 | 1.63 | 1.49 | 0.14 |
| 126.7 | 92.8 | 2.48 | 2.02 | 0.46 |
| 165.6 | 96.7 | 5.13 | 5.16 | −0.03 |

The differences between the humidities calculated from the psychrometer and those calculated from the humidity probe are given in the last column of the table. These differences average only 6% based on humidity and only 0.44 C.° based on wet bulb temperature of gas flow. Thus, these experimental results show that the instant psychrometer can accurately measure humidity at high temperatures.

It will be apparent to those skilled in the art that numerous changes and modifications can be made in the preferred psychrometer of the invention just described. Accordingly, the foregoing description is to be interpreted in an illustrative and not in a limitative sense, the scope of the invention being defined solely by the appended claims.

We claim:

1. A psychrometer for measuring the humidity of a gas flow, comprising:
a first sensor for measuring the dry bulb temperature of said gas flow;
a second sensor for measuring the wet bulb temperature of said gas flow;
a wick surrounding said second sensor and capable of absorbing a volatile liquid;
liquid supply means for supplying said volatile liquid to said wick adjacent said second sensor; and
liquid preheater means for heating said volatile liquid to a temperature within about 5 C.° of said wet bulb temperature sensed by said second sensor before said liquid is supplied to said liquid supply means.

2. A psychrometer according to claim 1 wherein said liquid preheater means heats said volatile liquid to a temperature with about 2 C.° of said wet bulb temperature.

3. A psychrometer according to claim 1 wherein:
said liquid preheater means comprises first preheater means for heating said liquid to a temperature within about 10 C.° of said wet bulb temperature and second preheater means for receiving liquid from said first preheater means and effecting heat exchange between said liquid and said gas flow.

4. A psychrometer according to claim 3 wherein said second preheater means comprises a conduit for said liquid, said conduit being disposed in said gas flow and having walls defining at least one aperture therethrough, and an auxiliary wick surrounding said conduit, such that part of said liquid passing said conduit will leave said conduit via said aperture, be absorbed by said wick and evaporated therefrom by said gas flow, thereby effecting said heat exchange between said liquid and said gas flow.

5. A psychrometer according to claim 1 wherein said liquid supply means comprises a hollow collar surrounding said wick, said collar having walls defining at least one aperture for egress of said fluid from the hollow interior of said collar into said wick.

6. A psychrometer according to claim 1 wherein a gas preheater is provided for heating said gas flow before contact thereof with said sensors.

7. A psychrometer according to claim 1 wherein gas flow control means are provided to ensure that the velocity of said gas flow past said first and second sensors is not less than about 1.5 meters/sec.

* * * * *